United States Patent
Bodner (10) Patent No.: US 12,226,609 B2
(45) Date of Patent: Feb. 18, 2025

(54) METHOD TO DETECT INADVERTENT DELIVERY OF DRUG TO A SUBCUTANEOUS POCKET

(71) Applicant: Medtronic, Inc., Minneapolis, MN (US)

(72) Inventor: Jeffrey P. Bodner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 849 days.

(21) Appl. No.: 17/247,561

(22) Filed: Dec. 16, 2020

(65) Prior Publication Data
US 2022/0184298 A1    Jun. 16, 2022

(51) Int. Cl.
A61M 5/142      (2006.01)
A61M 5/168      (2006.01)

(52) U.S. Cl.
CPC .... *A61M 5/14276* (2013.01); *A61M 5/16809* (2013.01); *A61M 2205/02* (2013.01); *A61M 2205/3324* (2013.01); *A61M 2205/3368* (2013.01); *A61M 2205/3553* (2013.01)

(58) Field of Classification Search
None
See application file for complete search history.

(56) References Cited

U.S. PATENT DOCUMENTS

| 4,360,019 A | 11/1982 | Portner et al. |
| 4,573,994 A | 3/1986 | Fischell et al. |
| 4,772,263 A | 9/1988 | Dorman et al. |
| 5,045,064 A | 9/1991 | Idriss |
| 5,085,644 A | 2/1992 | Watson et al. |
| 5,217,442 A | 6/1993 | Davis |
| 5,281,210 A | 1/1994 | Burke et al. |
| 5,527,307 A | 6/1996 | Srisathapat et al. |
| 5,702,372 A | 12/1997 | Nelson |
| 5,833,654 A | 11/1998 | Powers et al. |

(Continued)

FOREIGN PATENT DOCUMENTS

| CN | 208838708 U | 5/2019 | |
| ES | 2267396 A1 * | 3/2007 | ............. A61B 90/04 |

(Continued)

OTHER PUBLICATIONS

Extended European Search Report for European Application No. 19202531.0, dated Jan. 27, 2020.

(Continued)

*Primary Examiner* — Jenna Zhang
(74) *Attorney, Agent, or Firm* — Husch Blackwell LLP (57) ABSTRACT

An implantable medical device configured to monitor fluid in proximity to an implantable medical device for an inadvertent introduction of infusate into a pocket of tissue surrounding the implantable medical device during a refill procedure, the implantable medical device including a refillable infusate delivery system, the refillable infusate delivery system including a reservoir in fluid communication with an access port, and a conductivity sensor configured to monitor fluid in proximity to the conductivity sensor for an introduction of infusate into a pocket of tissue surrounding the implantable medical device, wherein the conductivity sensor comprises a pair of electrodes positioned on an external surface of the implantable medical device.

23 Claims, 7 Drawing Sheets

(56) References Cited

U.S. PATENT DOCUMENTS

| | | | |
|---|---|---|---|
| 5,957,890 | A | 9/1999 | Mann et al. |
| 6,013,051 | A | 1/2000 | Nelson |
| 6,042,579 | A | 3/2000 | Elsberry et al. |
| 6,283,943 | B1 | 9/2001 | Dy et al. |
| 6,572,583 | B1 | 6/2003 | Olsen et al. |
| 6,579,280 | B1 | 6/2003 | Kovach et al. |
| 6,852,106 | B2 | 2/2005 | Watson et al. |
| 6,962,577 | B2 | 11/2005 | Tallarida et al. |
| 6,962,580 | B2 | 11/2005 | Adams et al. |
| 7,072,802 | B2 | 7/2006 | Hartlaub |
| 7,351,239 | B2 | 4/2008 | Gill |
| 7,366,562 | B2 | 4/2008 | Dukesherer et al. |
| 7,637,897 | B2 | 12/2009 | Ginggen |
| 7,803,143 | B2 | 10/2010 | Tallarida et al. |
| 7,942,863 | B2 | 5/2011 | Kalpin et al. |
| 7,963,956 | B2 | 6/2011 | Kunst |
| 8,320,991 | B2 | 11/2012 | Jascob et al. |
| 8,419,710 | B2 | 4/2013 | Keimel et al. |
| 8,483,802 | B2 | 7/2013 | Kalpin et al. |
| 8,545,484 | B2 | 10/2013 | Haase et al. |
| 8,591,456 | B2 | 11/2013 | Steinbach |
| 8,613,724 | B2 | 12/2013 | Lanier, Jr. et al. |
| 8,721,605 | B2 | 5/2014 | Brandt et al. |
| 8,915,893 | B2 | 12/2014 | Steinbach |
| 8,932,271 | B2 | 1/2015 | Hamatake et al. |
| 9,079,004 | B2 | 7/2015 | Wiley et al. |
| 9,122,785 | B2 | 9/2015 | Alme et al. |
| 9,421,325 | B2 | 8/2016 | Kalpin |
| 9,427,553 | B2 | 8/2016 | Nelson |
| 9,433,764 | B2 | 9/2016 | East et al. |
| 9,744,338 | B2 | 8/2017 | East et al. |
| 9,782,536 | B2 | 10/2017 | Skutnik et al. |
| 9,919,102 | B2 | 3/2018 | John |
| 9,981,117 | B2 | 5/2018 | Brandt et al. |
| 9,993,600 | B2 | 6/2018 | Lanier, Jr. et al. |
| 10,238,851 | B2 | 3/2019 | Butziger et al. |
| 10,376,635 | B2 | 8/2019 | Haase |
| 10,589,024 | B2 | 3/2020 | John |
| 10,596,362 | B2 | 3/2020 | Fielder et al. |
| 10,625,060 | B2 | 4/2020 | Børgesen |
| 11,147,918 | B2 | 10/2021 | Christensen |
| 2005/0124980 | A1 | 6/2005 | Sanders |
| 2005/0137537 | A1 | 6/2005 | Watson et al. |
| 2005/0277912 | A1* | 12/2005 | John ............... A61M 5/16827 604/890.1 |
| 2006/0089619 | A1 | 4/2006 | Ginggen |
| 2006/0089620 | A1 | 4/2006 | Gibson |
| 2007/0078391 | A1* | 4/2007 | Wortley ........... A61M 39/0208 604/116 |
| 2007/0112291 | A1 | 5/2007 | Børgesen |
| 2008/0243074 | A1* | 10/2008 | Miesel ............. A61M 5/16859 604/111 |
| 2008/0243093 | A1 | 10/2008 | Kalpin et al. |
| 2009/0192404 | A1* | 7/2009 | Ortiz ................... A61B 5/4238 600/547 |
| 2010/0030196 | A1 | 2/2010 | Hildebrand et al. |
| 2011/0301575 | A1 | 12/2011 | Miesel et al. |
| 2012/0053514 | A1 | 3/2012 | Robinson et al. |
| 2013/0116665 | A1* | 5/2013 | Humayun ............ A61M 5/162 604/891.1 |
| 2014/0228765 | A1 | 8/2014 | Burke et al. |
| 2016/0089521 | A1 | 3/2016 | Dragoon et al. |
| 2016/0354540 | A1 | 12/2016 | Kalpin |
| 2017/0043151 | A1 | 2/2017 | Bellrichard et al. |
| 2017/0325685 | A1 | 11/2017 | Shachar et al. |
| 2018/0117243 | A1 | 5/2018 | Maguire |
| 2019/0009014 | A1 | 1/2019 | Chen et al. |
| 2019/0060565 | A1 | 2/2019 | Gyory |
| 2019/0184139 | A1 | 6/2019 | Nelson et al. |
| 2019/0269850 | A1 | 9/2019 | Shih et al. |
| 2020/0061362 | A1 | 2/2020 | Singh et al. |
| 2020/0121849 | A1 | 4/2020 | Christensen |
| 2020/0121850 | A1 | 4/2020 | Christensen |
| 2020/0155003 | A1* | 5/2020 | Mitchell ............... A61B 5/1118 |

FOREIGN PATENT DOCUMENTS

| | | |
|---|---|---|
| WO | WO0066204 A1 | 11/2000 |
| WO | WO2009129474 A1 | 10/2009 |
| WO | WO2012138854 A1 | 10/2012 |
| WO | WO 2013/052414 | 4/2013 |
| WO | WO2013134486 A4 | 9/2013 |
| WO | WO2016059162 A1 | 4/2016 |
| WO | WO2020046791 A1 | 3/2020 |

OTHER PUBLICATIONS

Alcyone Lifesciences, Inc., Bringing Hope to Spinal Muscular Atrophy (SMA) Patients with the Alcyone Lifesciences ThecaFlex DRx™ System Breakthrough Device, Dec. 2, 2019, 3 pages, available at: https://www.prnewswire.com/news-releases/bringing-hope-to-spinal-muscular-atrophy-sma-patients-with-the-alcyone-lifesciences-thecaflex-drx-system-breakthrough-device-300967222.html.

Application and File history for U.S. Appl. No. 16/168,358, filed Oct. 23, 2018. Inventors: Christenson et al.

Application and File history for U.S. Appl. No. 16/168,399, filed Oct. 23, 2018. Inventors: Christenson et al.

Application and File history for U.S. Appl. No. 17/085,562, filed Oct. 30, 2020. Inventors: Bodner.

* cited by examiner

METHOD TO DETECT INADVERTENT DELIVERY OF DRUG TO A SUBCUTANEOUS POCKET

TECHNICAL FIELD

The present technology is generally related to implantable medical devices, and more particularly to implantable medical pumps and ports for managing the delivery and dispensation of prescribed therapeutic agents.

BACKGROUND

Implantable medical devices, such as implantable medical pumps and ports, are useful in managing the delivery and dispensation of prescribed therapeutic agents, nutrients, drugs, infusates such as antibiotics, blood clotting agents, analgesics and other fluid or fluid like substances (collectively "infusates" or "infusates") to patients in volume- and time-controlled doses as well as through boluses. Such implantable pumps and ports are particularly useful for treating diseases and disorders that require regular or chronic (i.e., long-term) pharmacological intervention, including tremor, spasticity, multiple sclerosis, Alzheimer's disease, Parkinson's disease, amyotrophic lateral sclerosis (ALS), Huntington's disease, cancer, epilepsy, chronic pain, urinary or fecal incontinence, sexual dysfunction, obesity, and gastroparesis, to name just a few. Depending upon their specific designs and intended uses, implantable pumps and ports are well adapted to administer infusates to specific areas within the vasculatures and central nervous system, including the subarachnoid, epidural, intrathecal, and intracranial spaces or provide access to those spaces for aspiration.

Providing access to the cerebrospinal fluid for the administration of infusates or aspiration of fluid has a number of important advantages over other forms of infusate administration. For example, oral administration is often not workable because the systematic dose of the substance needed to achieve the therapeutic dose at the target site may be too large for the patient to tolerate without adverse side effects. Also, some substances simply cannot be absorbed in the gut adequately for a therapeutic dose to reach the target site. Moreover, substances that are not lipid soluble may not cross the blood-brain barrier adequately if needed in the brain. In addition, infusion of substances from outside the body requires a transcutaneous catheter or access with a hypodermic needle, which results in other risks such as infection or catheter dislodgment. Further, implantable pumps avoid the problem of patient noncompliance, namely the patient failing to take the prescribed drug or therapy as instructed.

Such implantable pumps and ports are typically implanted at a location within the body of a patient (typically a subcutaneous region in the lower abdomen) and are connected to a catheter configured to deliver infusate to a selected delivery site in the patient. The catheter is generally configured as a flexible tube with a lumen running the length of the catheter to a selected delivery site in the body, such as the intracranial or subarachnoid space.

Implantable medical pumps and ports of this type often include an expandable fluid reservoir, which is accessible for refill or aspiration through an access port. During the refill process, it is important that the infusate not be inadvertently injected directly into the body of the patient, as a potentially fatal overdose may occur. For example, if the portion of the refilling apparatus employed to deliver the infusate is not properly positioned within the access port, the infusate can be injected directly into a pocket surrounding the implantable pump or port.

SUMMARY OF THE DISCLOSURE

The techniques of this disclosure generally relate to systems and method configured to reduce the risk of inadvertently introducing infusate into the pocket of tissue immediately surrounding the implantable pump or port (occasionally referred to herein as a "pocket fill") during a refill procedure. Pocket fill during refill of an implantable pump or port generally presents one of the largest risks associated with targeted drug delivery, and has the potential to result in patient death. Over the years, various approaches have been developed to reduce the likelihood or hazards associated with a pocket fill. One such approach is to use one or more positioning markers to improve identification of the access port. Examples of such systems and methods are described in U.S. patent application Ser. No. 16/803,269 (disclosing contactless alignment between the refill apparatus and the access port) and U.S. patent application Ser. No. 17/085,562 (disclosing wireless access port location), both of which are assigned to Medtronic Inc., the contents of which are hereby incorporated by reference herein in their entirety.

Another approach to inhibit the likelihood of a pocket fill is to employ needle detection sensor technology to confirm proper placement of the refilling apparatus within the access port. Examples of such systems and methods are described in U.S. Pat. No. 5,171,228 (disclosing needle detection via a resonant circuit); U.S. Pat. No. 6,740,076 (disclosing needle detection via an ultrasonic transducer); U.S. Pat. Nos. 7,942,863; 8,535,280; & 8,920,389 (disclosing needle detection via pressure changes); U.S. Pat. No. 10,143,796 (disclosing needle detection via a voltmeter, ammeter, ohmmeter, pressure sensor, flow sensor, capacitive sensor, acoustic sensor, and/or optical sensor); and U.S. patent application Ser. Nos. 16/168,358; 16/168,399 (disclosing needle insertion responsive systems and methods), all of which are assigned to Medtronic Inc., the contents of which are hereby incorporated by reference herein in their entirety.

Yet another approach to inhibit the likelihood of a pocket fill is to employ reservoir volume sensing technology to provide confirmation of a flow fluid into the reservoir during the refill process. Examples of such systems and methods are described in U.S. Pat. No. 6,482,177 (disclosing the use of an inductance coil to determine a reservoir volume); U.S. Pat. No. 6,542,350 (disclosing the use of a capacitor to determine reservoir volume); U.S. Pat. Nos. 9,421,325; 9,687,603; 8,810,394; & 9,814,833 (disclosing the use of pressure sensors to determine if flow rate and/or change in volume); U.S. Pat. No. 8,708,959 (disclosing the use of a variable resistor to determine a reservoir volume); U.S. Pat. Nos. 8,206,378; 8,206,378 & 8,512,286 (disclosing the use of a known pressure or change in pressure to determine a reservoir volume); and U.S. Pat. No. 8,801,668 (disclosing the use of pump noises to determine a reservoir volume), all of which are assigned to Medtronic Inc., the contents of which are hereby incorporated by reference herein in their entirety.

Although such approaches have been effective in reducing the likelihood of or hazards associated with an inadvertent pocket fill during the refill procedure, there is an ever present desire to further improve and enhance safety associated with targeted drug delivery. Embodiments of the present disclosure take a new approach to alerting caregivers of the possibility of a pocket fill through the use of a conductivity sensor arrangement mounted on exterior of the implantable pump or port to detect the inadvertent introduction of infusate into tissue surrounding the implantable pump or port. In some embodiments, such conductivity sensor arrangement can be paired with positioning markers to improve identification of the access port, needle detection sensor technology to confirm proper placement of the refilling apparatus within the access port, and/or reservoir volume sensing technology to provide confirmation of a flow fluid into the reservoir during the refill process, thereby creating even safer targeted drug delivery systems.

One embodiment of the present disclosure provides an implantable medical device, including a refillable infusate delivery system, the refillable infusate delivery system including a reservoir in fluid communication with an access port, and a conductivity sensor configured to monitor fluid in proximity to the conductivity sensor for an inadvertent injection of infusate into a pocket of tissue surrounding the implantable medical device, wherein the conductivity sensor comprises a pair of electrodes positioned on an external surface of the implantable medical device.

In one embodiment, the pair of electrodes are constructed of a platinum iridium material. In one embodiment, each of the pair of electrodes has a diameter of between about 1 mm and about 3 mm. In one embodiment, the pair of electrodes are at least partially surrounded by an insulative material, thereby insulating the pair of electrodes from a metallic external surface of the implantable medical device. In one embodiment, the implantable medical device includes a first pair of electrodes positioned on a top surface of the implantable medical device, and a second pair of electrodes positioned on an opposite, bottom surface of the implantable medical device. In one embodiment, the implantable medical device is at least one of an implantable infusion pump or an implantable port. In one embodiment, the implantable medical device further comprises at least one of an access port marker to improve identification of the access port, a needle detector to confirm proper placement of a refilling apparatus within the access port, and a reservoir fill sensor to aid in positioning of a refilling device relative to the implantable medical device. In one embodiment, implantable medical device further includes a physiological sensor configured to provide a confirmation of an inadvertent injection of infusate into a pocket of tissue surrounding the implantable medical device through a monitoring of one or more physiological conditions of a patient into which the implantable medical device is implanted.

Another embodiment of the present disclosure provides a medical system including an implantable medical device comprising an infusate delivery system and at least one electrical conductivity sensor configured to monitoring for an inadvertent injection of infusate into a pocket of tissue surrounding the implantable medical device, wherein the conductivity sensor comprises a pair of electrodes positioned on an external surface of the implantable medical device, the pair of electrodes configured to infer a salinity of fluid in proximity to the pair of electrodes.

In one embodiment, the implantable medical device is at least one of an implantable infusion pump or an implantable port. In one embodiment, the implantable medical device includes a first pair of electrodes positioned on a top surface of the implantable medical device, and a second pair of electrodes positioned on an opposite, bottom surface of the implantable medical device. In one embodiment, the implantable medical device further comprises at least one of an access port marker to improve identification of the access port, a needle detector to confirm proper placement of a refilling apparatus within the access port, and a reservoir fill sensor to aid in positioning of a refilling device relative to the implantable medical device. In one embodiment, the medical system further includes a physiological sensor configured to provide a confirmation of an inadvertent injection of infusate into a pocket of tissue surrounding the implantable medical device through a monitoring of one or more physiological conditions of a patient into which the implantable medical device is implanted. In one embodiment, the medical system further includes an external programmer in wireless communication with the implantable medical device. In one embodiment, the external programmer is configured to activate the at least one electrical conductivity sensor from an inactive state. In one embodiment, the medical system further includes an external physiological sensor in wireless communication with at least one of the external programmer or implantable medical device the external physiological sensor configured to provide a confirmation of an inadvertent injection of infusate into a pocket of tissue surrounding the implantable medical device through a monitoring of one or more physiological conditions of a patient into which the implantable medical device is implanted.

Yet another embodiment of the present disclosure provides a method of monitoring fluid in proximity to an implantable medical device for an inadvertent injection of infusate into a pocket of tissue surrounding the implantable medical device, the method including: activating a conductivity sensor; obtaining a baseline conductivity measurement; establishing a triggering threshold conductivity value; and initiating at least one of an alarm, alert or notification upon a conductivity value sensed by the conductivity sensor meeting or exceeding the triggering threshold conductivity value.

In one embodiment, the conductivity sensor is activated via an external programmer upon initiation of a refill procedure in one embodiment, the method further includes activating at least one of an access port marker to improve identification of the access port, a needle detector to confirm proper placement of a refilling apparatus within the access port, and a reservoir fill sensor to aid in positioning of a refilling device relative to the implantable medical device. In one embodiment, the method further includes monitoring a physiological sensor, the physiological sensor configured to provide a confirmation of an inadvertent injection of infusate into a pocket of tissue surrounding the implantable medical device.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 1:
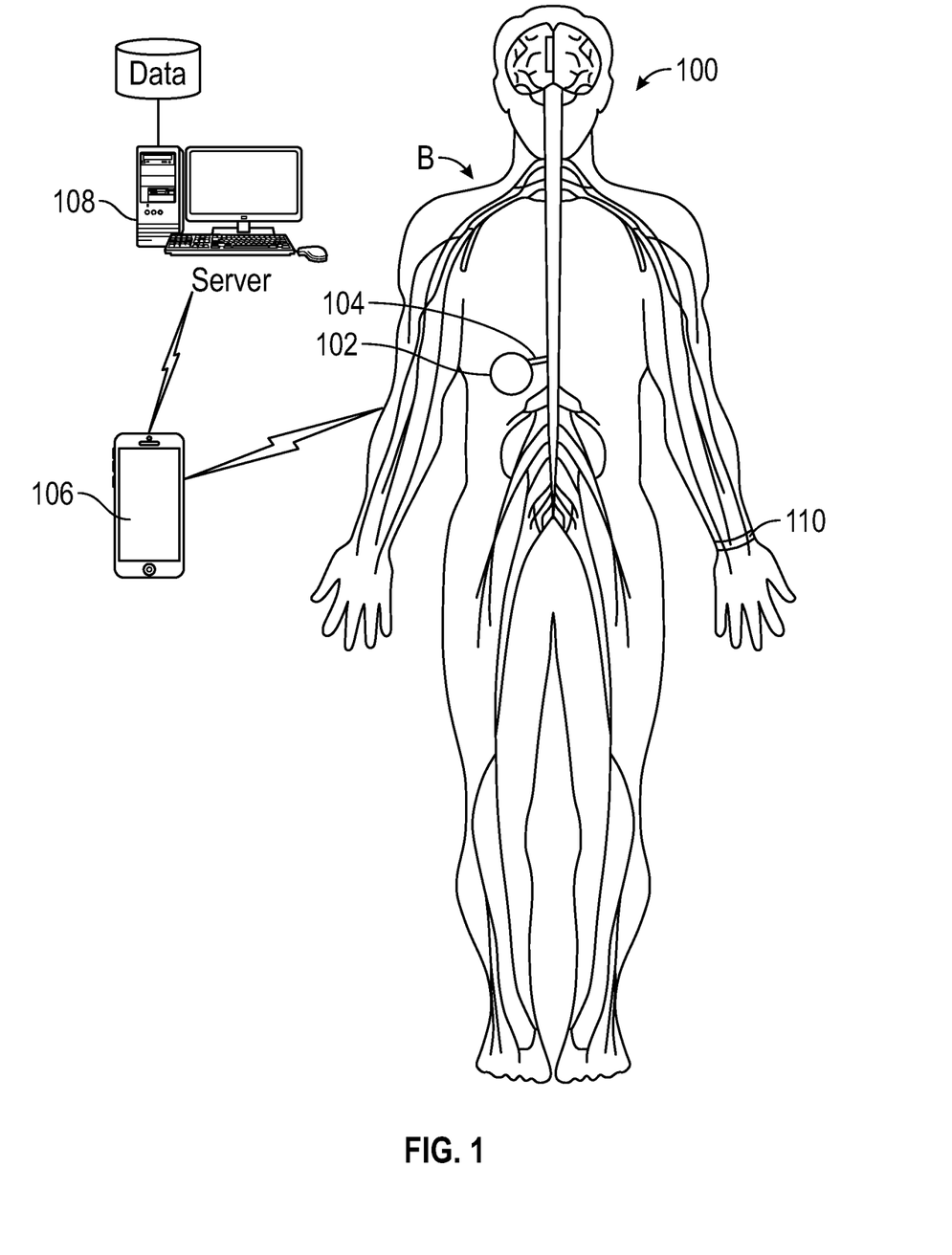
FIG. 1 is a schematic view depicting a medical system configured to alert caregivers to the possibility of an inadvertent injection of infusate directly into tissue (or a void or pocket between tissue layers) in proximity to an implantable medical device, in accordance with an embodiment of the disclosure.

Referring to FIG. 1, a medical system 100 configured to alert caregivers to the possibility of an inadvertent injection of infusate directly into tissue surrounding an implantable medical device 102 is depicted in accordance with an embodiment of the disclosure. The medical system 100 can include an implantable catheter 104, which in some embodiments can be in fluid communication with the implantable medical device, which can be either of an implantable pump or port. As depicted, the implantable device 102 can be implanted within the body B of a patient, for example, in an interior torso cavity or in proximity to the patient's ribs or cranially for the introduction of infusate into the patient (e.g., within an intrathecal space, intracranial space, pulmonary artery, etc.) for targeted delivery of infusate. In some embodiments, the implantable device 102 can be placed subcutaneously, and can be held in position by sutures or other retaining features.

In some embodiments, the medical system 100 can further include an optional external programmer 106 and optional server 108 configured to communicate with the implantable device 102. In some embodiments, the programmer 106 can be a handheld, wireless portable computing device, such as a cellular telephone, tablet, dedicated implantable device programmer, or the like. Further, in some embodiments, the medical system 100 can include one or more external physiological sensors 110, which can be in communication with the implantable device 102, optional external programmer 106, and optional server 108. In one embodiment, one or more physiological sensors 110 can be incorporated into implantable device 102 or external programmer 106. In one embodiment, a physiological sensor 110 can be worn by the patient (e.g., a smart watch, wristband tracker, sensors embedded in clothing, etc.), carried by the patient (e.g., a smart phone, mobile computing device, etc.), or positioned in proximity to the patient (e.g., a stationary monitor, etc.). Examples of physiological sensors 110 include a heart rate monitor, pulse oximeter, respiratory sensor, perspiration sensor, posture orientation sensor, motion sensor, accelerometer, or the like.

Figure 2A:
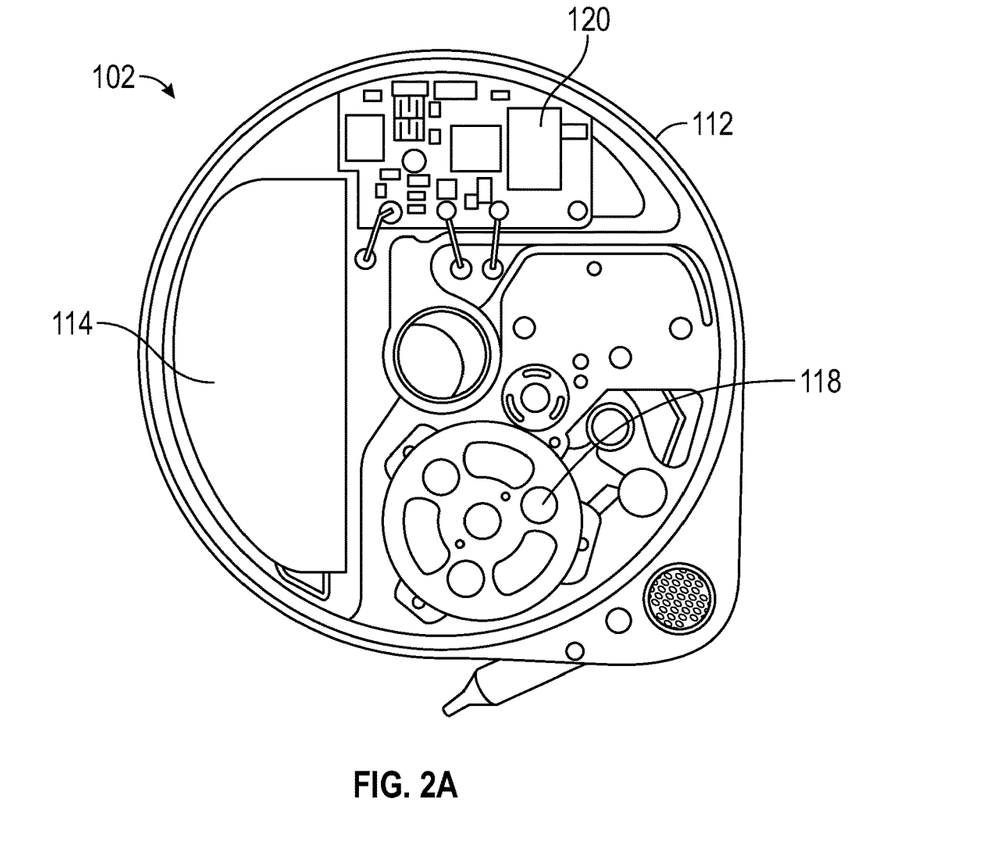
FIG. 2A is a top cross-sectional view depicting an implantable device configured to alert users to the possibility of a pocket fill, in accordance with an embodiment of the disclosure.
Figure 2B:
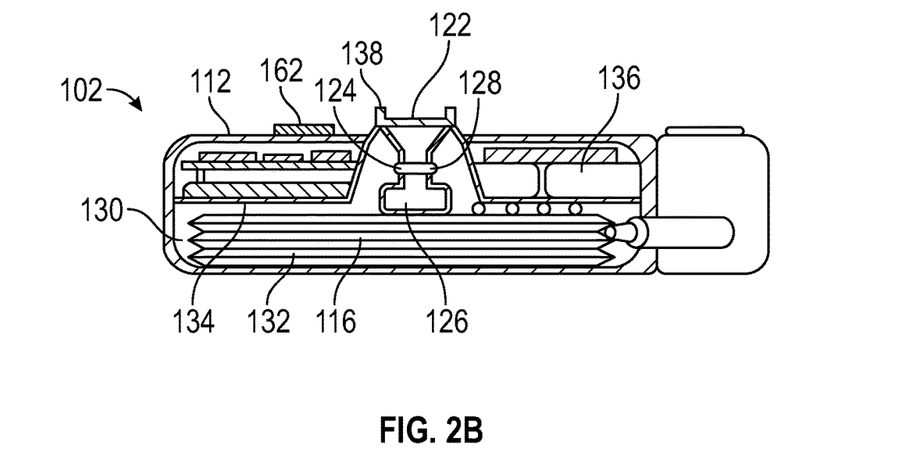
FIG. 2B is a side cross-sectional view depicting the implantable device of FIG. 2A.

Referring to FIGS. 2A-B, cross sectional views of an implantable device 102 configured to alert caregivers to the possibility of a pocket fill are depicted in accordance with an embodiment of the disclosure. The implantable device 102 can generally include a housing 112, power source 114, reservoir 116, pump 118, and computing device 120. The housing 112 can be constructed of a material that is biocompatible and hermetically sealed, such as titanium, tantalum, stainless steel, plastic, ceramic, or the like.

The reservoir 116 can be carried by the housing 112 and can be configured to contain infusate. In one embodiment, infusate within the reservoir 116 can be accessed via an access port 122. Accordingly, the access port 122 can be utilized to refill, aspirate, or exchange fluid within the reservoir 116. In some embodiments, the access port 122 can include one or more positional markers 138, for example in the form of a tactile protrusion, one or more lights or LEDs to illuminate through tissue of the patient, an acoustic device to at least confirm location of the access port 122, and/or one or more wireless location/orientation sensors to aid in positioning of a refilling device relative to the implantable device 102.

In some embodiments, the access port 122 can include a septum 124 configured to seal a port chamber 126 relative to an exterior of the housing 112. The septum 124 can be constructed of a silicone rubber or other material having desirable self-sealing and longevity characteristics. The port chamber 126 can be in fluid communication with the reservoir 116. In one embodiment, the access port 122 can further include an optional needle detection sensor 128, for example in the form of a mechanical switch, resonant circuit, ultrasonic transducer, voltmeter, ammeter, ohmmeter, pressure sensor, flow sensor, capacitive probe, acoustic sensor, and/or optical sensor configured to detect and confirm the presence of an injection needle of a refilling apparatus.

The reservoir 116 can include a flexible diaphragm 130. The flexible diaphragm 130, alternatively referred to as a bellows, can be substantially cylindrical in shape and can include one or more convolutions configured to enable the flexible diaphragm 130 to expand and contract between an extended or full position and an empty position. In one embodiment, the flexible diaphragm 130 can divide the reservoir 116 into an infusate chamber 132 containing liquid infusate (within the flexible diaphragm 130), and a vapor chamber 134 (surrounding the flexible diaphragm 130).

As the infusate chamber 132 is filled with infusate, the flexible diaphragm 130 extends downwardly (with reference to FIG. 2B) toward a bottom portion of the housing 112 until it has reached a maximum volume or some other desired degree of fullness. Alternatively, as the infusate chamber 132 is aspirated, the flexible diaphragm 130 contracts upwardly toward a top portion of the housing 112 until the infusate chamber reaches a minimum volume. In one embodiment, the flexible diaphragm 130 can have a compression spring rate which tends to naturally bias the flexible diaphragm 130 towards an expanded position.

In one embodiment, the implantable medical pump 102 can optionally include a reservoir volume sensor 136, for example in the form of an inductance coil, capacitive probe, pressure sensor, acoustic sensor, and/or optical sensor/infrared (IR) transducer configured to detect the expansion/contraction of the flexible diaphragm 130. Accordingly, the fill sensor 136 can be utilized to measure a dimension of the reservoir 116 for the purpose of confirming a flow of infusate into the reservoir 116 during a refill procedure.

The pump 118 can be carried by the housing 112. The pump 118 can be in fluid communication with the reservoir 116 and can be in electrical communication with the computing device 120. The pump 118 can be any pump sufficient for infusing to the patient, such as a peristaltic pump, piston pump, a pump powered by a stepper motor or rotary motor, a pump powered by an AC motor, a pump powered by a DC motor, electrostatic diaphragm, piezoelectric motor, solenoid, shape memory alloy, or the like.

Figure 3:
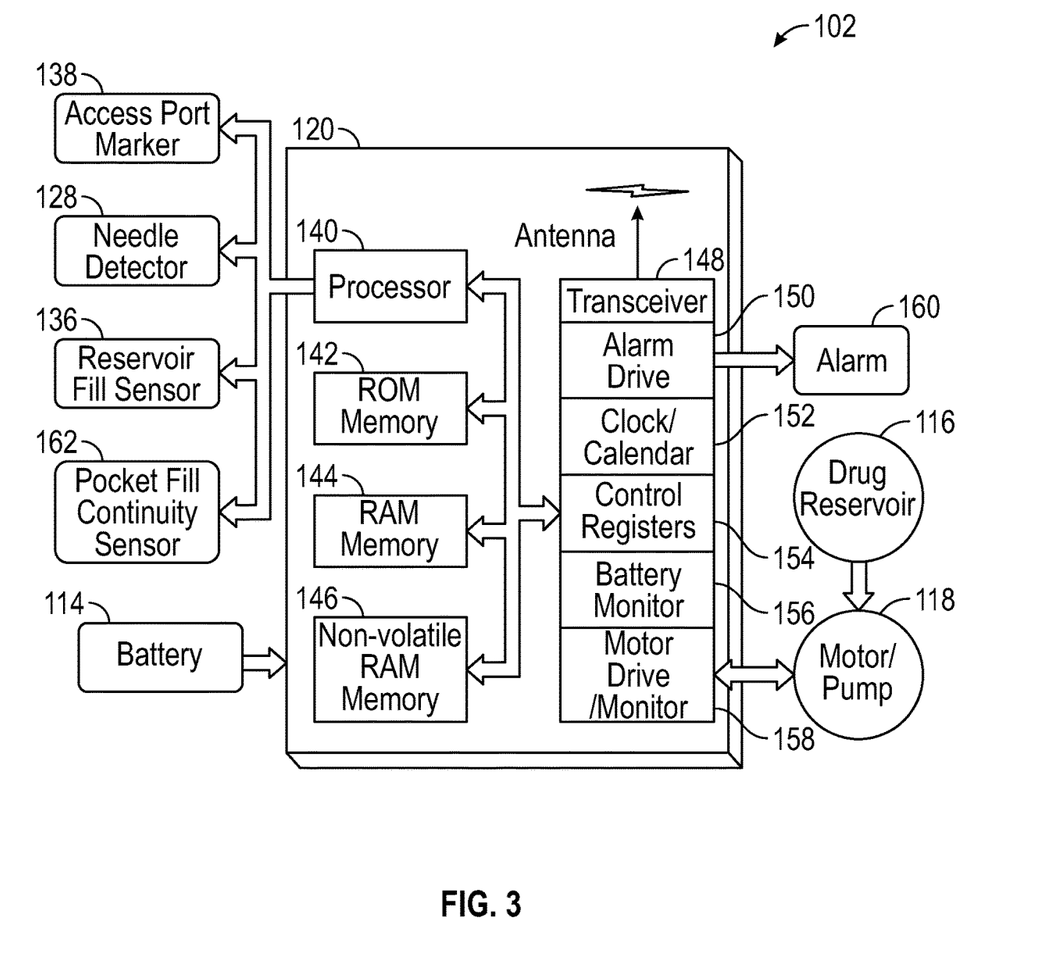
FIG. 3 is a block diagram of an implantable device configured to alert caregivers to the possibility of a pocket fill is depicted, in accordance with an embodiment of the disclosure.

Referring to FIG. 3, a block diagram of an implantable device 102 configured to alert caregivers to the possibility of a pocket fill is depicted in accordance with an embodiment of the disclosure. The computing device 120 can be carried in the housing 112 (as depicted in FIG. 2A) and can be in electrical communication with the pump 118, and power source 114. The power source 114 can be a battery, such as a rechargeable lithium-ion battery. The power source 114, which can be monitored via the battery monitor 156, can be carried in the housing 112, and can selectively operate the pump 118, and computing device 120. Control of the pump 118 can be directed by a motor drive/monitor element 158.

The computing device 120 can include a processor 140, memory 142, 144 & 146, and transceiver circuitry 148. In one embodiment, the processor 140 can be a microprocessor, logic circuit, Application-Specific Integrated Circuit (ASIC) state machine, gate array, controller, or the like. The computing device 120 can generally be configured to control infusion of infusate according to programmed parameters or a specified treatment protocol. The programmed parameters or specified treatment protocol can be stored in the memory 142, 144 & 146 for specific implementation by a control register 154. A clock/calendar element 152 can maintain system timing for the computing device 120. In one embodiment, an alarm drive 150 can be configured to activate one or more notification, alert or alarm features, such as an illuminated, auditory or vibratory alarm 160.

The transceiver circuitry 148 can be configured to receive information from and transmit information to the one or more physiological sensors 110, external programmer 106, and server 108. The implantable device 102 can be configured to receive programmed parameters and other updates from the external programmer 106, which can communicate with the implantable device 102 through well-known techniques such as wireless telemetry, Bluetooth, or one or more proprietary communication schemes (e.g., Tel-M, Tel-C, etc.). In some embodiments, the external programmer 106 can be configured for exclusive communication with one or more implantable device 102. In other embodiments, the external programmer 106 can be any computing platform, such as a mobile phone, tablet or personal computer. In some embodiments, the implantable device 102 and external programmer 106 can further be in communication with a cloud-based server 108. The server 108 can be configured to receive, store and transmit information, such as program parameters, treatment protocols, drug libraries, and patient information, as well as to receive and store data recorded by the implantable device 102.

Figure 4:
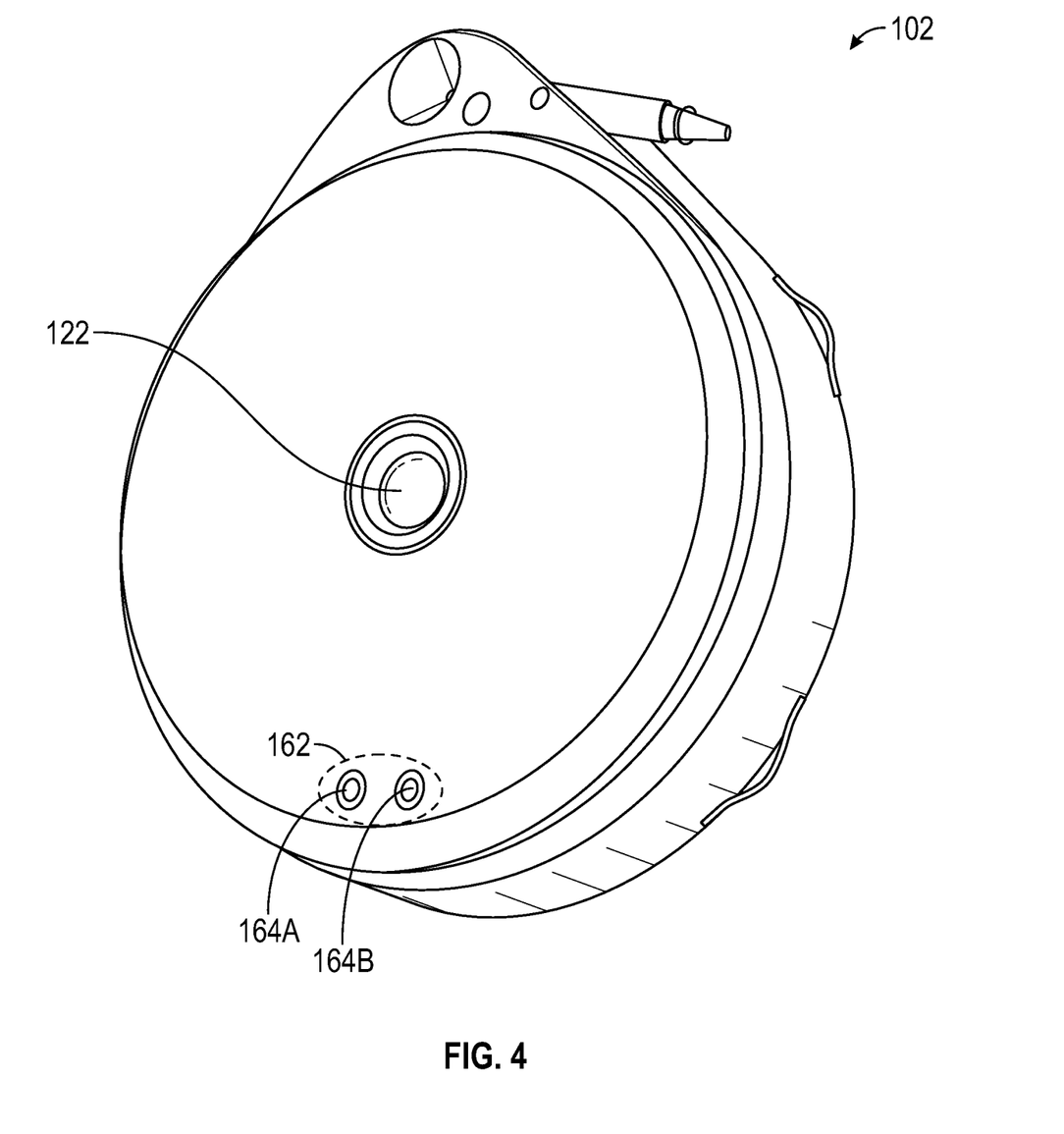
FIG. 4 is a perspective view depicting an implantable device including one or more detectors or sensors configured to sense one or more conditions of fluid surrounding the implantable device, in accordance with an embodiment of the disclosure.

With additional reference to FIG. 4, in some embodiments, the implantable device 102 can include one or more detector 162 comprising two or more electrodes 164A & 164B positioned on the next interior of the housing 112 configured to sense a salinity in the fluid and tissue surrounding the housing 112 in proximity to the electrodes 164A/B. As depicted in FIG. 3, the one or more detector 162 can be in communication with the processor 140, thereby enabling the detector 162 to be selectively activated during a refill process. For example, upon commencing the refill process, a clinician can select a refill process workflow from on a user interface of the external programmer 106. The external programmer 106 can communicate with the implantable device 102 via the transceiver 148, thereby activating the detector 162, as well as other sensors and markers (e.g., needle detection sensor 128, fill sensor 136, and access port marker 138) prior to a physical attempt to insert a needle of the refill device into the access port 122 of the implantable device 102.

Figure 5:
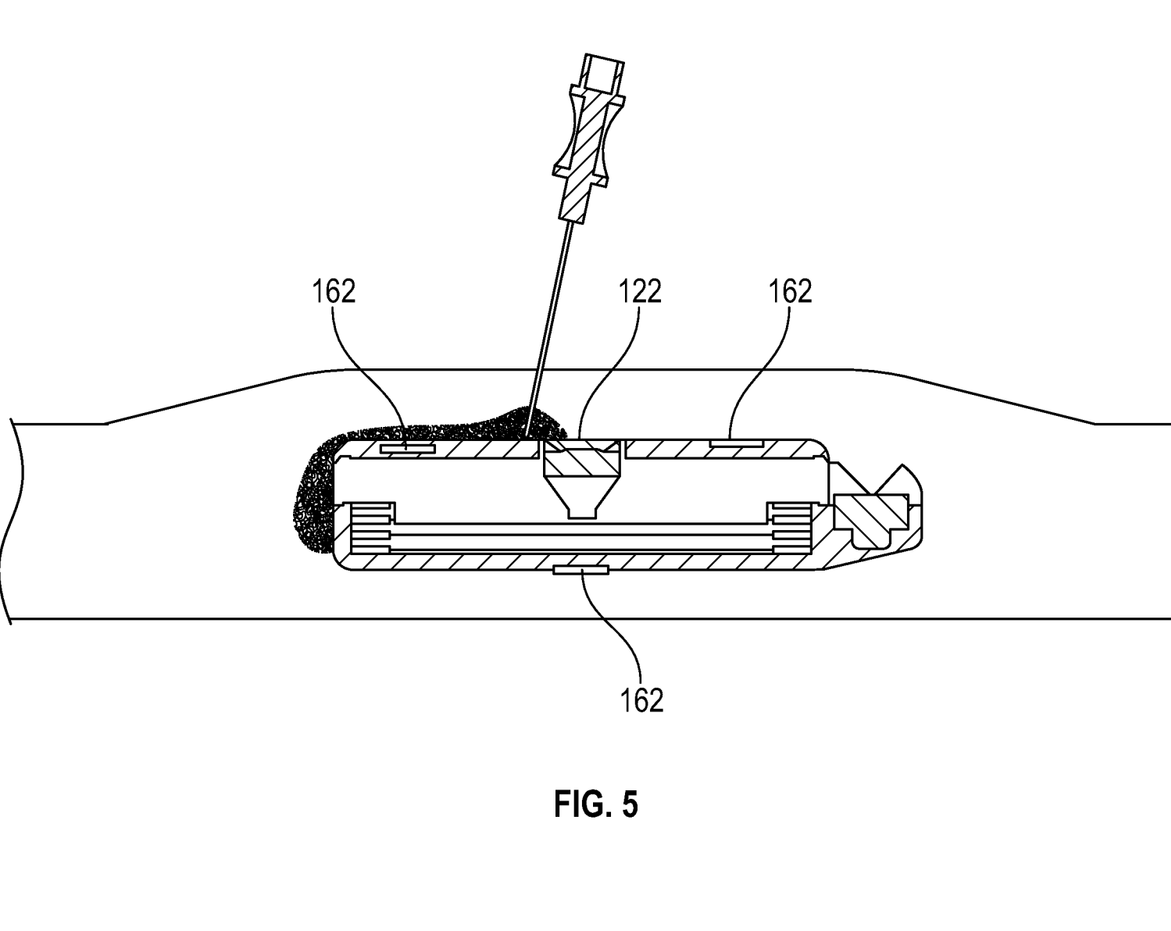
FIG. 5 is a schematic view depicting the detection of an inadvertent introduction of infusate in the pocket surrounding an implantable medical device during a refill procedure, in accordance with an embodiment of the disclosure.

With additional reference to FIG. 5, once activated, the detector 162 can be used to sense an electrical conductivity between pairs of electrodes 164A/B. In some embodiments, the detector 162 can be configured to sense a pH, temperature, or other condition of fluid in proximity to the detector 162 (either alone or in combination). Thereafter, if an infusate (particularly a saline-based infusate) is introduced into the pocket between tissue layers surrounding the implantable device 102, the electrodes 164A/B will immediately detect a change in a condition of the fluid in proximity to the detector 162, which can be used to initiate an alert or alarm 160, thereby immediately notifying the clinician that a pocket fill may be occurring.

In some embodiments, the electrodes 164A/B can be constructed of a conductive platinum-iridium material, surrounded by hermetically sealed insulative ceramic material within the housing 112; although the use of other materials is also contemplated. In some embodiments, the electrodes 164A/B can measure between about 1 mm and about 3 mm in diameter; although the electrodes of other shapes and sizes are also contemplated. In one embodiment, the implantable device 102 can include multiple detectors 162 including corresponding pairs of electrodes 164A/B. For example, in one embodiment, the implantable device 102 can include at least one detector 162 on an upper surface of the implantable device 102 and at least one detector 162 on a bottom surface of the implantable device 102; although the positioning of a greater or lesser number of detectors 162 in locations other than the top and bottom surface of the implantable device 102 is also contemplated.

Figure 6:
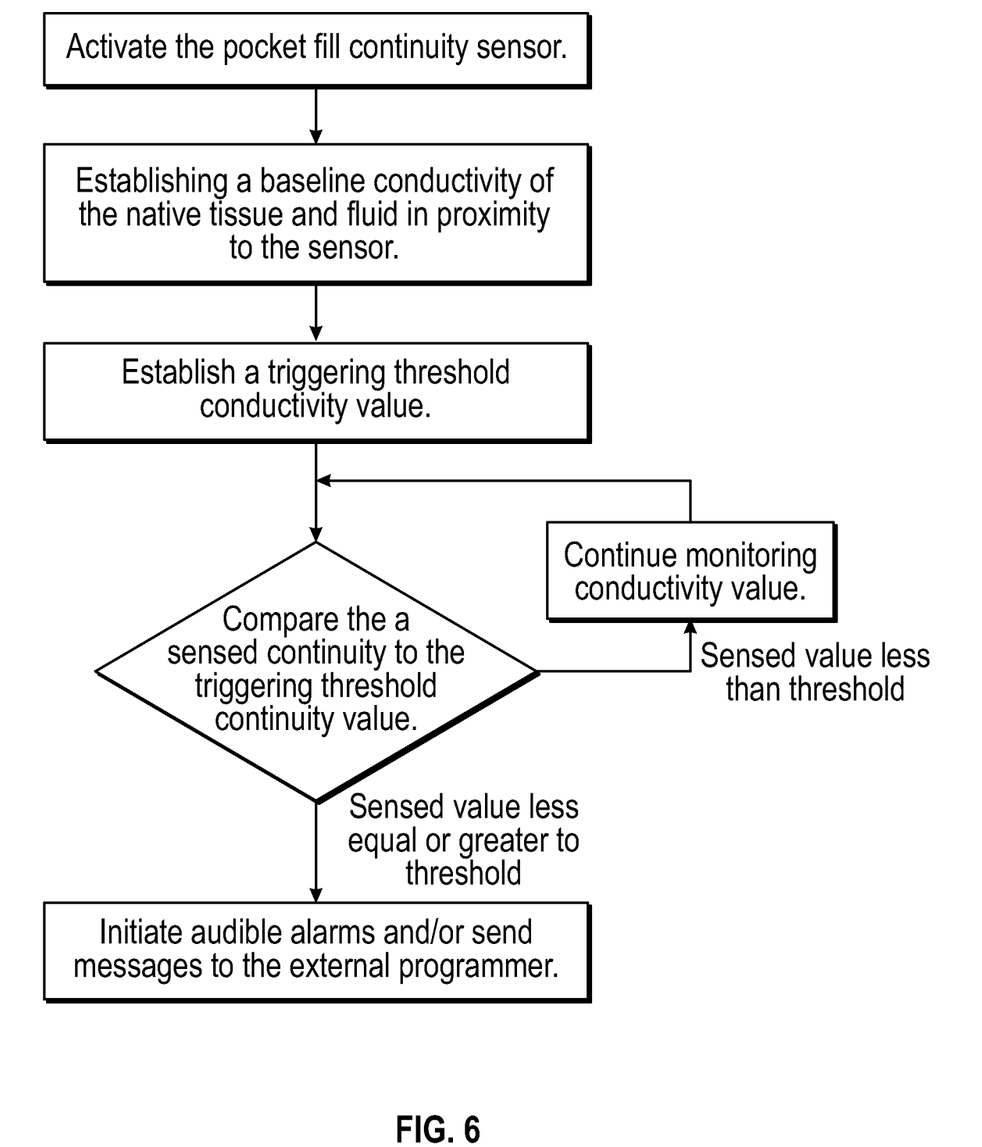
FIG. 6 is a flowchart depicting a method of monitoring for the possibility of an inadvertent injection of infusate directly into tissue surrounding an implantable medical device, in accordance with an embodiment of the disclosure.

Referring to FIG. 6, a method 200 of monitoring for the possibility of an inadvertent injection of infusate directly into tissue surrounding an implantable medical device 102 is depicted in accordance with an embodiment of the disclosure. At S202, the detector 162 can be activated by the computing device 120 prior to initiating the physical steps associated with the refill procedure. Upon activation, at S204, the detector 162 can obtain a baseline conductivity measurement, thereby establishing a baseline conductivity of the native tissue and fluid in proximity to the electrodes 164A/B (e.g., absent the presence of any fluid introduced during the refill procedure). At S206, the baseline conductivity measurement can be used to establish a triggering threshold conductivity value. Once the refill process begins, at S208, electrical conductivity can be sensed continuously or on a rapid periodic basis for comparison to the baseline. At S210, an increase in sensed conductivity equal or greater to the triggering threshold conductivity value can initiate audible alarms and/or send messages to the external programmer, thereby alerting users that a pocket fill may be occurring.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Figure 7A:
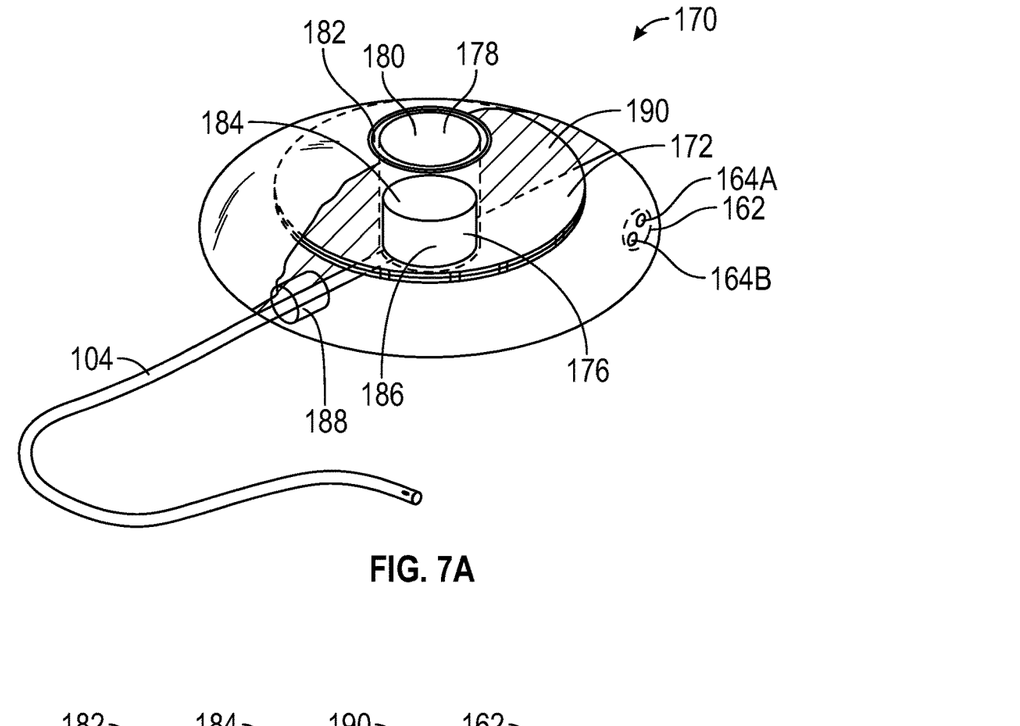
FIG. 7A is a perspective view depicting an implantable port including one or more detectors or sensors configured to sense one or more conditions of fluid surrounding the implantable port, in accordance with an embodiment of the disclosure.

With reference to FIG. 7A, in some embodiments, the one or more detectors 162 (e.g., including electrodes 164A/B) can be used in conjunction with an implantable port 170, for example, in a system 100 (such as that depicted in FIG. 1) in place of an implantable medical pump 102. Aside from replacement of a pump 102 with an implantable port 170, other components of the medical system 100 can remain the same. Various embodiments of the present invention will be described in detail with reference to the drawings, wherein like reference numerals represent like parts and assemblies throughout the several views.

Figure 7B:
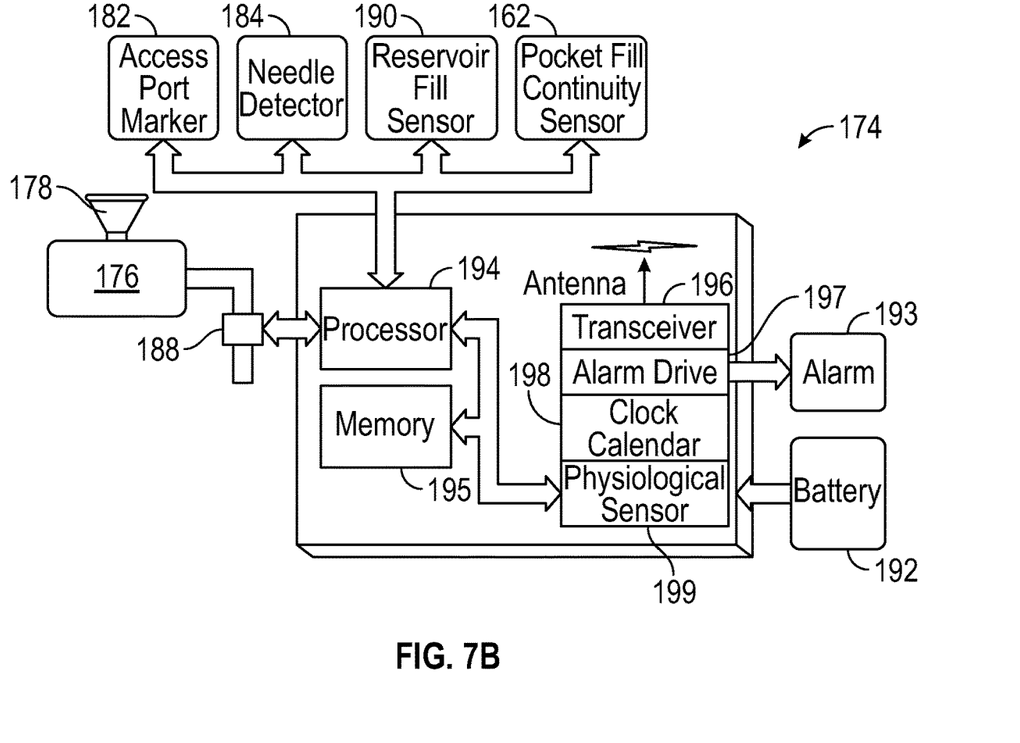
FIG. 7B is a block diagram of an implantable port configured to alert caregivers to the possibility of a pocket fill is depicted, in accordance with an embodiment of the disclosure.

In one embodiment, the implantable port 170 can include a housing 172, electrical circuitry 174 (as depicted in FIG. 7B), and a reservoir 176. The housing 172 can be constructed of a material that is biocompatible and hermetically sealed, such as titanium, tantalum, stainless steel, plastic, ceramic, or the like. The reservoir 176 can be carried by the housing 172 and can be configured to contain an infusate. In one embodiment, infusate within the reservoir 176 can be accessed via an access port 178, including a self-sealing septum 180 positioned beneath the skin of the patient. Accordingly, the access port 178 can be utilized to refill fluid within the reservoir 176, thereby enabling the implantable port 170 to be recharged with infusate after use. Additionally, the access port 178 can be utilized to aspirate or exchange fluid within the implantable port 170, thereby enabling the aspiration (e.g., prior to an Mill procedure) or replacement of infusate (e.g., medicament with an expiration date) without a need to explant the implantable port 170 from the patient.

In some embodiments, the access port 178 can include one or more positional markers 182, for example in the form of a tactile protrusion, one or more lights or LEDs to illuminate through tissue of the patient, an acoustic device to at least confirm location of the access port 122, and/or one or more wireless location/orientation sensors to aid in positioning of a refilling device relative to the implantable port 170. Additionally, in some embodiments, the access port 178 can include an optional needle detection sensor 184, for example in the form of a mechanical switch, resonant circuit, ultrasonic transducer, voltmeter, ammeter, ohmmeter, pressure sensor, flow sensor, capacitive probe, acoustic sensor, and/or optical sensor configured to detect and confirm the presence of an injection needle of a refilling apparatus.

In some embodiments, the reservoir 176 can include a flexible diaphragm 186, configured to enable the reservoir 176 to be expanded between an extended or full position and an empty position. In some embodiments, the flexible diaphragm 186 can include a spring or other mechanism configured to naturally bias the reservoir 176 to the empty position. In such embodiments, the flexible diaphragm 186 can be expanded to the extended position by the introduction of pressurized infusate into the reservoir 176. In some embodiments, the implantable port 170 can optionally include a reservoir volume sensor 190, for example in the form of an inductance coil, capacitive probe, pressure sensor, acoustic sensor, and/or optical sensor/infrared (IR) transducer configured to detect the expansion/contraction of the flexible diaphragm 186. Accordingly, the reservoir volume sensor 190 can be utilized to measure a dimension of the reservoir 176 for the purpose of confirming a flow of infusate into the reservoir 176 during a refill procedure.

In embodiments with a pressurized reservoir 176, the implantable port 170 can include a delivery valve 188, configured such that opening of the valve 188 causes infusate within the pressurized reservoir 176 to be expelled under a natural bias of the flexible diaphragm 186. Accordingly, embodiments of the present disclosure provide a simple drug delivery mechanism without the need for a medicament pump, flow regulation, monitoring of drug delivery, or the like. In some embodiments the implantable port 170 can be configured to deliver medicament directly into tissue of the patient surrounding the implantable port 170, without the need for a catheter. In other embodiments, the implantable port 170 can be the operably coupled to a catheter 104 for targeted delivery of medicament into a specific area of the patient.

Referring to FIG. 7B, a block diagram of an implantable port 170 configured to alert caregivers to the possibility of a pocket fill is depicted in accordance with an embodiment of the disclosure. The electrical circuitry 174 can be carried in the housing 172 and can be powered by a power source 192. The power source 192 can be a battery, such as a rechargeable lithium-ion battery. The electrical circuitry 174 can include one or more physiological sensors 199, processor 194, memory 195, and transceiver circuitry 196. The one or more physiological sensors 199 can include a heart rate sensor, respiration sensor, pulse oximeter, blood pressure sensor, intracranial pressure sensor, cerebral spinal fluid pressure sensor, intra-abdominal pressure sensor, temperature sensor, or the like. In embodiments including a reservoir 176, a medicament delivery valve 188 can be connected to or in communication with the electrical circuitry 174.

The processor 194 can be a microprocessor, logic circuit, Application-Specific Integrated Circuit (ASIC) state machine, gate array, controller, or the like. The transceiver circuitry 196 can be configured to receive information from and transmit information an external programmer 106 and server 108 through well-known techniques such as wireless telemetry, Bluetooth, or one or more proprietary communication schemes (e.g., Tel-M, Tel-C, etc.). In some embodiments, the electrical circuitry 174 can further include clock/calendar element 198 configured to maintain system timing, and an alarm drive 197 configured to activate one or more notification, alert or alarm features, such as an illuminated, auditory or vibratory alarm 193.

In some embodiments, the detector 162 can be activated by the electrical circuitry 174 prior to initiating the physical steps associated with the refill procedure. Upon activation, the detector 162 can obtain a baseline measurement, thereby establishing a baseline measurement of the native tissue and fluid in proximity to the electrodes 164A/B (e.g., absent the presence of any fluid introduced during the refill procedure). The baseline conductivity measurement can be used to establish a triggering threshold conductivity value. Once the refill process begins, one or more condition can be monitored for comparison to the baseline. a change in the monitored condition equal or greater to the triggering threshold value can initiate audible alarms and/or send messages to the external programmer, thereby alerting users that a pocket fill may be occurring.

In some embodiments, the detector 162 can be used in conjunction with at least one of an access port positional marker 182, needle detection sensor 184, reservoir volume sensor 190, or physiological sensor 199 thereby creating a safer system 100 configured to directly address the risks associated with implantable device refills.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An implantable medical device, comprising:
    a refillable infusate delivery system, the refillable infusate delivery system comprising a reservoir in fluid communication with an access port;
    two or more exterior sensors positioned on an external surface of the implantable medical device and configured to monitor fluid in proximity to an exterior of the implantable medical device for an injection of infusate into a pocket of tissue surrounding the implantable medical device during a procedure to refill the reservoir with infusate when the reservoir is empty; and
    a processor configured to monitor the two or more exterior sensors during infusate refill procedures and to activate one or more notification, alert or alarm features to notify a user that a pocket fill may be occurring.

2. The implantable medical device of claim 1, wherein the two or more exterior sensors comprise at least one of one or more electrodes, one or more pH sensors, one or more temperature sensors, or a combination thereof.

3. The implantable medical device of claim 1, wherein the two or more exterior sensors comprise a pair of electrodes constructed of a platinum iridium material positioned on the exterior of the implantable medical device.

4. The implantable medical device of claim 1, wherein the two or more exterior sensors comprise at least one electrode having a diameter of between about 1 mm and about 3 mm.

5. The implantable medical device of claim 1, wherein the two or more exterior sensors comprise an electrode at least partially surrounded by an insulative material to insulate the electrode from a metallic external surface of the implantable medical device.

6. The implantable medical device of claim 1, wherein the two or more exterior sensors comprise a first sensor positioned on a first surface of the implantable medical device, and a second sensor positioned on a second surface of the implantable medical device.

7. The implantable medical device of claim 1, wherein the implantable medical device is at least one of an implantable infusion pump or an implantable port.

8. The implantable medical device of claim 1, wherein the implantable medical device further comprises at least one of an access port marker to improve identification of the access port, a needle detector to confirm proper placement of a refilling apparatus within the access port, and a reservoir fill sensor to aid in positioning of a refilling device relative to the implantable medical device.

9. The implantable medical device of claim 1, further comprising a physiological sensor configured to provide a confirmation of an introduction of infusate into a pocket of tissue surrounding the implantable medical device through a monitoring of one or more physiological conditions of a patient into which the implantable medical device is implanted.

10. A medical system, comprising:
    an implantable medical device comprising an infusate delivery system; two or more exterior sensors positioned on an external surface of the implantable medical device and configured to monitor fluid in proximity to an exterior of the implantable medical device for an injection of infusate into a pocket of tissue surrounding the implantable medical device during a procedure to refill the device with infusate when the device is empty; and a processor configured to monitor the two or more exterior sensors during infusate refill procedures and to activate one or more notification, alert or alarm features to notify a user that a pocket fill may be occurring.

11. The medical system of claim 10, wherein the two or more exterior sensors comprise at least one of one or more electrodes, one or more pH sensors, one or more temperature sensors, or a combination thereof.

12. The medical system of claim 10, wherein the implantable medical device is at least one of an implantable infusion pump or an implantable port.

13. The medical system of claim 10, wherein the two or more exterior sensors comprise a first sensor positioned on a first surface of the implantable medical device, and a second sensor positioned on a second surface of the implantable medical device, the first and second surface being exterior of the implantable medical device.

14. The medical system of claim 10, wherein the implantable medical device further comprises at least one of an access port marker to improve identification of an access port of the implantable medical device, a needle detector to confirm proper placement of a refilling apparatus within an access port of the implantable medical device, and a reservoir fill sensor to aid in positioning of a refilling device relative to the implantable medical device.

15. The medical system of claim 10, further comprising a physiological sensor configured to provide a confirmation of an introduction of infusate into a pocket of tissue surrounding the implantable medical device through a monitoring of one or more physiological conditions of a patient into which the implantable medical device is implanted.

16. The medical system of claim 10, further comprising an external programmer in wireless communication with the implantable medical device.

17. The medical system of claim 16, wherein the external programmer is configured to activate the two or more exterior sensors from an inactive state.

18. The medical system of claim 10, further comprising an external physiological sensor in wireless communication with at least one of the external programmer or implantable medical device, the external physiological sensor configured to provide a confirmation of an introduction of infusate into a pocket of tissue surrounding the implantable medical device through a monitoring of one or more physiological conditions of a patient into which the implantable medical device is implanted.

19. A method of monitoring fluid in proximity to an implantable medical device for an inadvertent injection of infusate into a pocket of tissue surrounding the implantable medical device during an infusate refill procedure, the method comprising:

activating two or more exterior sensors positioned on an external surface of the implantable medical device and configured to monitor fluid in proximity to an exterior of the implantable medical device;

obtaining a baseline measurement;

establishing a triggering threshold value; and initiating at least one of an alarm, alert or notification upon a measurement sensed by the two or more exterior sensors meeting or exceeding the triggering threshold value.

20. The method of claim 19, wherein the two or more exterior sensors comprise at least one of one or more electrodes, one or more pH sensors, one or more temperature sensors, or a combination thereof.

21. The method of claim 19, wherein the two or more exterior sensors are activated via an external programmer upon initiation of a refill procedure.

22. The method of claim 19, further comprising activating at least one of an access port marker to improve identification of the access port, a needle detector to confirm proper placement of a refilling apparatus within the access port, and a reservoir fill sensor to aid in positioning of a refilling device relative to the implantable medical device.

23. The method of claim 19, further comprising monitoring a physiological sensor, the physiological sensor configured to provide a confirmation of an introduction of infusate into a pocket of tissue surrounding the implantable medical device.

* * * * *